(12) United States Patent
Hofstetter

(10) Patent No.: US 7,670,321 B2
(45) Date of Patent: Mar. 2, 2010

(54) SEALING ELEMENT

(75) Inventor: Michael Hofstetter, Zollikofen (CH)

(73) Assignee: TecPharma Licensing AG, Burgdorf (CH)

( * ) Notice: Subject to any disclaimer, the term of this patent is extended or adjusted under 35 U.S.C. 154(b) by 1154 days.

(21) Appl. No.: 11/003,024

(22) Filed: Dec. 2, 2004

(65) Prior Publication Data

US 2005/0121856 A1    Jun. 9, 2005

(30) Foreign Application Priority Data

Dec. 5, 2003  (DE) .............................. 103 56 838

(51) Int. Cl.
  *A61M 5/00*  (2006.01)
  *H02K 11/00*  (2006.01)
  *H02K 5/10*  (2006.01)
(52) U.S. Cl. ........................... 604/207; 310/71; 310/87
(58) Field of Classification Search ................ 604/207, 604/890.1, 131; 417/410.1; 310/71, 87–89
  See application file for complete search history.

(56) References Cited

U.S. PATENT DOCUMENTS 5,334,799 A * 8/1994 Naito et al. ............. 174/17 VA
5,822,192 A   10/1998 Hayashi
7,264,611 B2 * 9/2007 Christenson et al. ........ 604/151

FOREIGN PATENT DOCUMENTS

| DE | 19817958   |   | 11/1999 |
|----|------------|---|---------|
| DE | 19948087   |   | 5/2001  |
| JP | 2002181754 | * | 6/2002  |
| JP | 2003152346 |   | 5/2003  |
| JP | 2003157740 |   | 5/2003  |

* cited by examiner

*Primary Examiner*—Kevin C Sirmons
*Assistant Examiner*—Elizabeth R Moulton
(74) *Attorney, Agent, or Firm*—Dorsey & Whitney LLP; David E. Bruhn, Esq.

(57) ABSTRACT

A sealing element for isolating or sealing off a component or structure of an injection or administering device from other components or structures of the device or from the surroundings, wherein the isolated component or structure is an electrical component. The invention encompasses methods of forming and using the sealing element, and an injection or administering device including the sealing element.

12 Claims, 3 Drawing Sheets

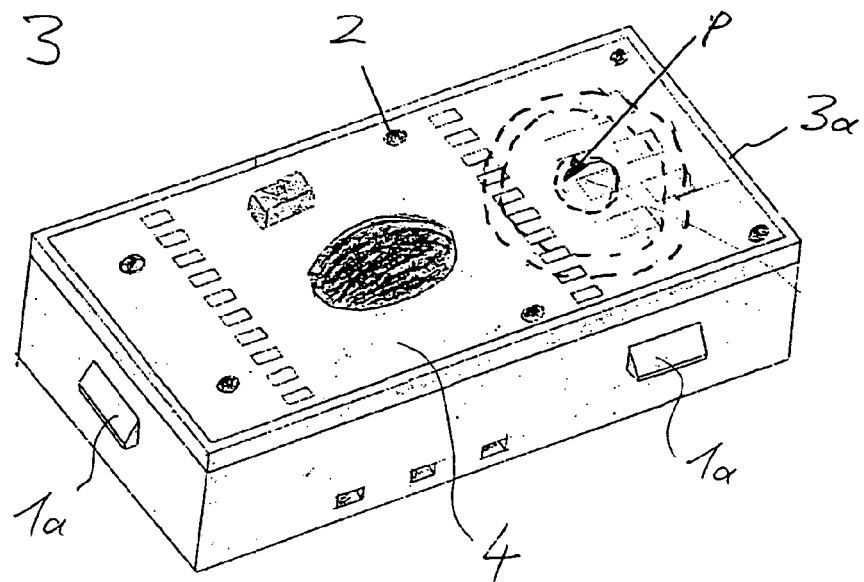
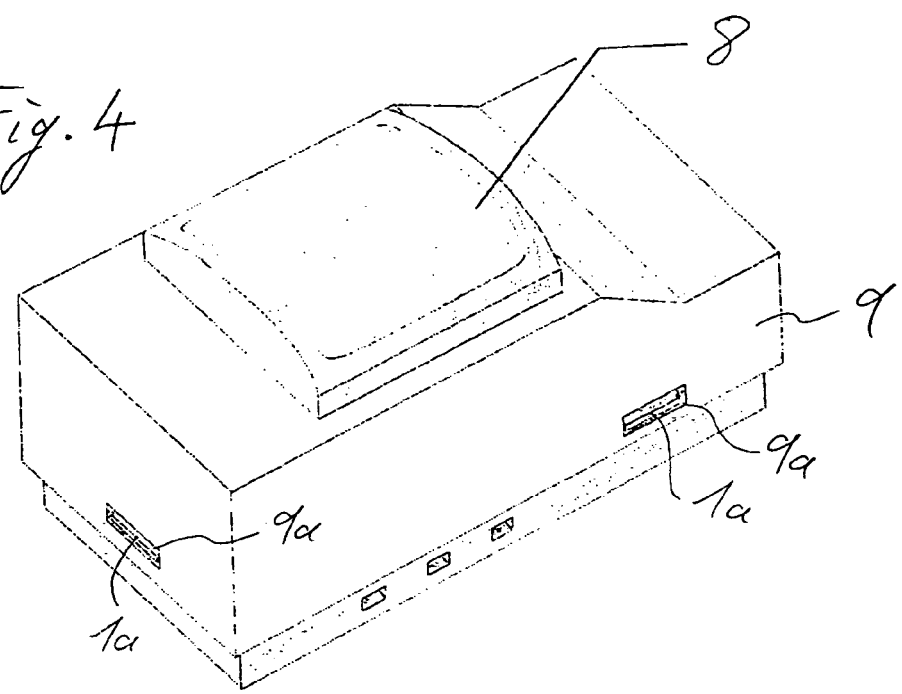

SEALING ELEMENT

CROSS-REFERENCE TO RELATED APPLICATIONS

This application claims priority to German Application No. DE 103 56 838.7, filed on Dec. 5, 2003, which is incorporated herein by reference.

BACKGROUND

The present invention relates to a seals, sealing elements, gaskets, stoppers and like structures and elements and their use for securing, closing and/or preventing the passage of substances. It further relates to devices and methods for administering medical or medicinal substances in doses, for example, injection and infusion devices, syringes, injection pens, etc. More particularly, it relates to a seal or sealing element for use in an injection device.

An embodiment of a known injection device is described in WO 03/053499, wherein FIG. 5 shows a rear portion of the injection device (a pen) in a longitudinal section. A piston rod K advances a piston (not shown) along the longitudinal axis L in the advancing direction (to the left in FIG. 5) towards a reservoir outlet (not shown), wherein the extent of the shift by the piston rod K is defined by rotating the setting element E and can be triggered by pressing the setting element E. In order to show a user which dosage he has set by rotating the setting element E, an indicating element A is provided on which the amount of a dosage set is shown, wherein the dosage set is ascertained on the basis of the movement of contact elements 10 which are pressed by one or more cam discs 11 which are also rotated by a rotational movement of the setting element E. If the cam discs 11 are suitably arranged, the succession of pressing and releasing the contact elements 10 by the cam discs 11 enables a determination as to how much the setting element E has been rotated, in order to indicate, on the indicating element A, a dosage or amount of active agent to be dispensed, set by the rotation.

However, a small amount of the substance to be dispensed by the device can penetrate, for example through openings provided for the contact elements 10, into the so-called E-module M or into the circuit or circuit board provided for evaluating the movement of the contact elements 10, and can damage the electronics. Equally, the electronics or the battery provided for operating the electronics can be compromised if such a device is stored in a refrigerator in order to ensure that the substance to be dispensed is optimally stored, wherein moisture can easily reach the electronics if the air is cooled and compressed.

SUMMARY

It is an object of the present invention to provide an injection device with a feature, structure or element which improves the fail-safe operation of the device It is another object of the present invention to provide a seal or sealing element for isolating one or more structures, features, components or operational parts of an injection device.

It is another object of the present invention to provide a sealing element for isolating one or more structures, features, components or operational parts of an injection device, for example, electrical components or drive components of the device, from other structures, features, components or operational parts of an injection device.

In one embodiment, the present invention comprises a sealing element for isolating or sealing off a component or structure of an injection or administering device from other components or structures of the device, wherein the isolated component or structure is, for example, an electrical component. The invention encompasses methods of forming and using the sealing element, and an injection or administering device including the sealing element.

In accordance with one embodiment of the invention, it is proposed to design a sealing element for an injection device such that at least one electronic or electrical component in the administering device or injection apparatus can be sealed off or isolated using said sealing element, wherein one or more batteries can preferably also be sealed off by the sealing element. In one embodiment, a contact pad provided for contact elements or pressure pieces is advantageously enlarged such that said contact pad can be used as a seal for electrical or electronic components and preferably also for sealing off a battery.

In the sense of the invention, the term "seal," and synonymous and similar terms, are to be understood as meaning any element or structure which, alone or in combination with one or more other elements or structures, such as a casing and/or a casing cover, can prevent a substance, for example a liquid such as a medicinal substance, water, etc., or a gas such as air, from being able to pass or penetrate into a particular space, such that the space and components in the space are protected from substances acting from without.

Thus, it is another object of the present invention to provide a seal element for isolating one or more structures, features, components or operational parts of an injection device, for example, receiving areas or cavities, or electrical components or drive components of the device, from other structures, features, components or operational parts of the device or from the surroundings or atmosphere around or inside the device.

In one embodiment, the sealing element in accordance with the invention is one piece or one part, i.e., is formed as or from a single element, in which, for example, partitioned spaces are provided in which components to be protected can be contained, lodged or housed. In some embodiments, the sealing element itself can be formed, completely or partially, for example on one surface, to be conductive, in order to enable the component enclosed by the sealing element to interact with the environment. In some embodiments, the sealing element can be completely or partially elastic or resiliently deformable in order to transfer an external pressure to produce a contact signal.

In some embodiments, a sealing element in accordance with the invention can also co-operate with one or more one-part or multiple-part casing elements of an injection device, in order to seal off components which are only partially encompassed by the casing, in order to protect the components arranged in the casing. As with the sealing element, in some embodiments, the casing or casing elements can be rigid or elastic and/or can be provided with a conductive property, such that components sealed off by the casing and/or the sealing element can interact with the environment or external elements. In some embodiments, the casing can be a so-called module base to which a contact pad is attached as a sealing element, so as to encompass a battery and/or circuit board. The casing or module base can then comprise one or more locking elements, for example in the form of locking projections, in order to be able to attach a module window and fixedly connect it to the module base, in order to be able to completely seal off one or more components. In some embodiments, the casing or module base can comprise one or more openings for pressure pieces and/or contact elements.

In embodiments wherein the sealing element is designed such that a battery compartment can be sealed off or integrated, then the battery can be protected from external substances, such as corrosive liquids. In some embodiments, if the sealing element, which may encompass the circuit board of an electrical circuit, is suitably configured, the battery can be connected directly to the circuit board by the sealing element, whereby elaborately attaching the battery, for example by soldering and providing contact bows, can be omitted. Advantageously, this makes the manufacturing process significantly simpler and cheaper and results in a lower susceptibility to faults.

In some preferred embodiments, a recess or cavity for a battery is provided in the sealing element, in combination with a conductive contact element such as a graphite keg, in order to be able to electrically connect areas of the battery which do not lie directly on a circuit board with the circuit board.

Advantageously, in some embodiments, at least one sensing element, such as one or more graphite pellets, is provided in conjunction with the sealing element, in order for example to deform the sealing element in the event of an external pressure on the sealing element, for example by a cam ring, and thus to press a sensing element or graphite pellet onto a circuit board, whereby an electrical contact on the circuit board is established, by which a signal generated by a cam disc can be detected and evaluated.

In some preferred embodiments, at least one venting channel is provided in the sealing element, such that the at least one sensing element can be easily moved back and forth, without being held in a position by an obtaining pressure or suction.

In some embodiments, the sealing element in accordance with the invention is preferably produced from an elastic or bending material, such as for example a suitable plastic, silicone or rubber, and can be completely or at least partially, for example on particular surface areas, conductive, whereby for example an electrical contact with the poles of a battery or with external components or in a circuit or circuit board sealed off by the sealing element can be established.

BRIEF DESCRIPTION OF THE DRAWINGS

FIG. 3 depicts a circuit board, placed on the sealing element shown in FIG. 2;

FIG. 4 depicts a module window, placed on the device shown in FIG. 3; and

DETAILED DESCRIPTION

Figure 1:
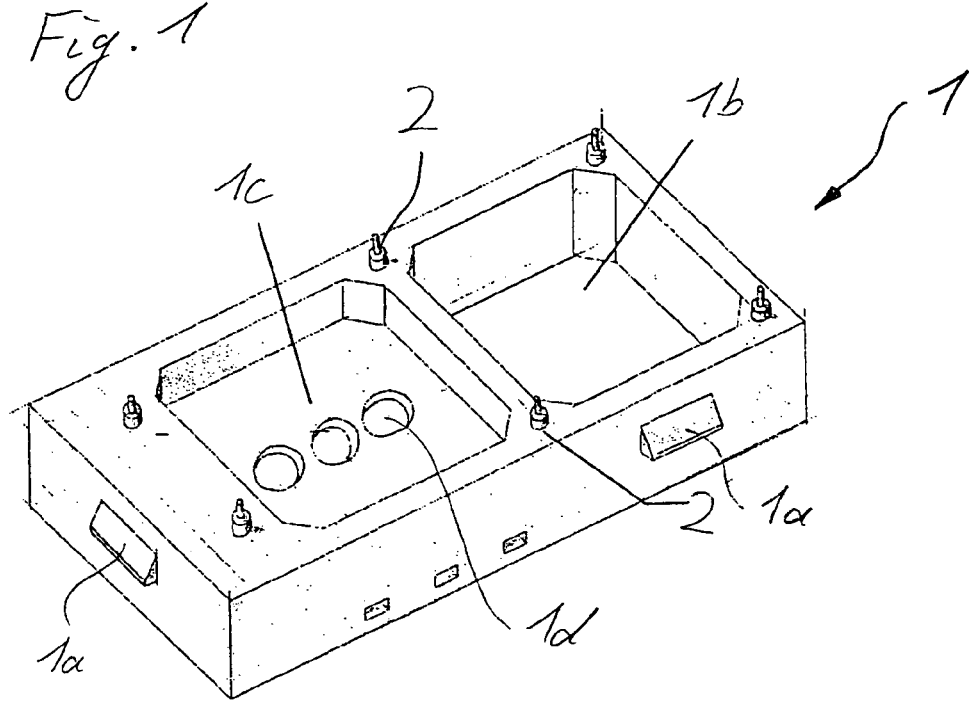
FIG. 1 depicts a module base.

FIG. 1 shows a module base 1 serving as a casing, in which locking projections 1a for locking to a module window casing 9 to be attached, shown in FIG. 4, are attached to the outer side. The interior of the module base 1 comprises two compartments or spaces 1b and 1c, wherein a battery, for example, can be inserted into the space 1b and the space 1c serves to transfer pressure movements by contact elements and/or pressure pieces 10 through holes 1d provided in the base of the module 1. Distancing bolts 2 are provided on the upper side of the module base 1, and a sealing element 3 and a circuit board 4 can be placed on said distancing bolts 2 as shown in FIGS. 2 and 3.

Figure 2:
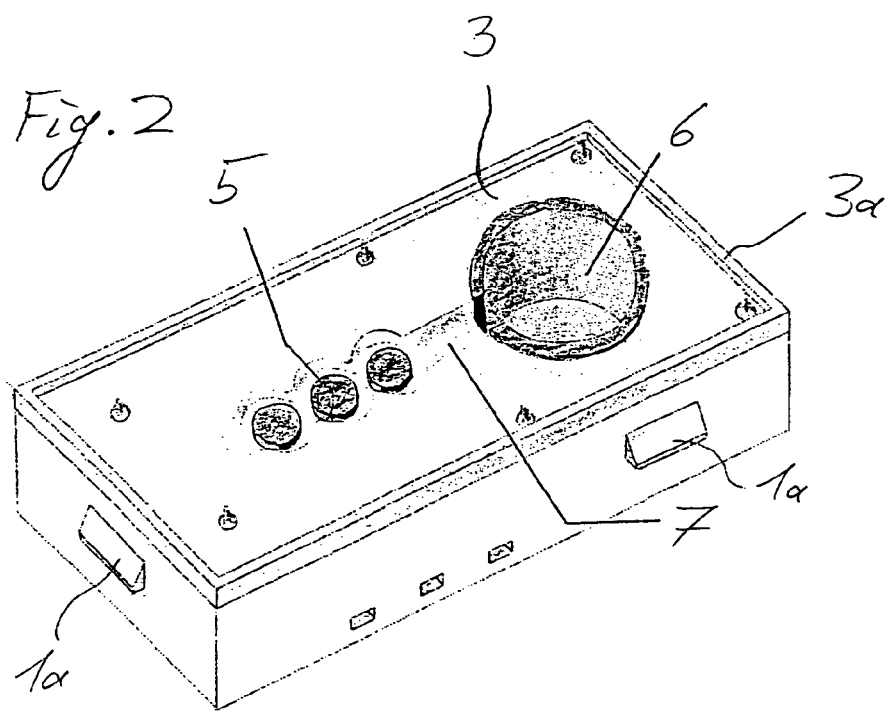
FIG. 2 depicts a silicone pad, placed on the module base as a sealing element, comprising graphite pellets and a graphite keg.
Figure 5:
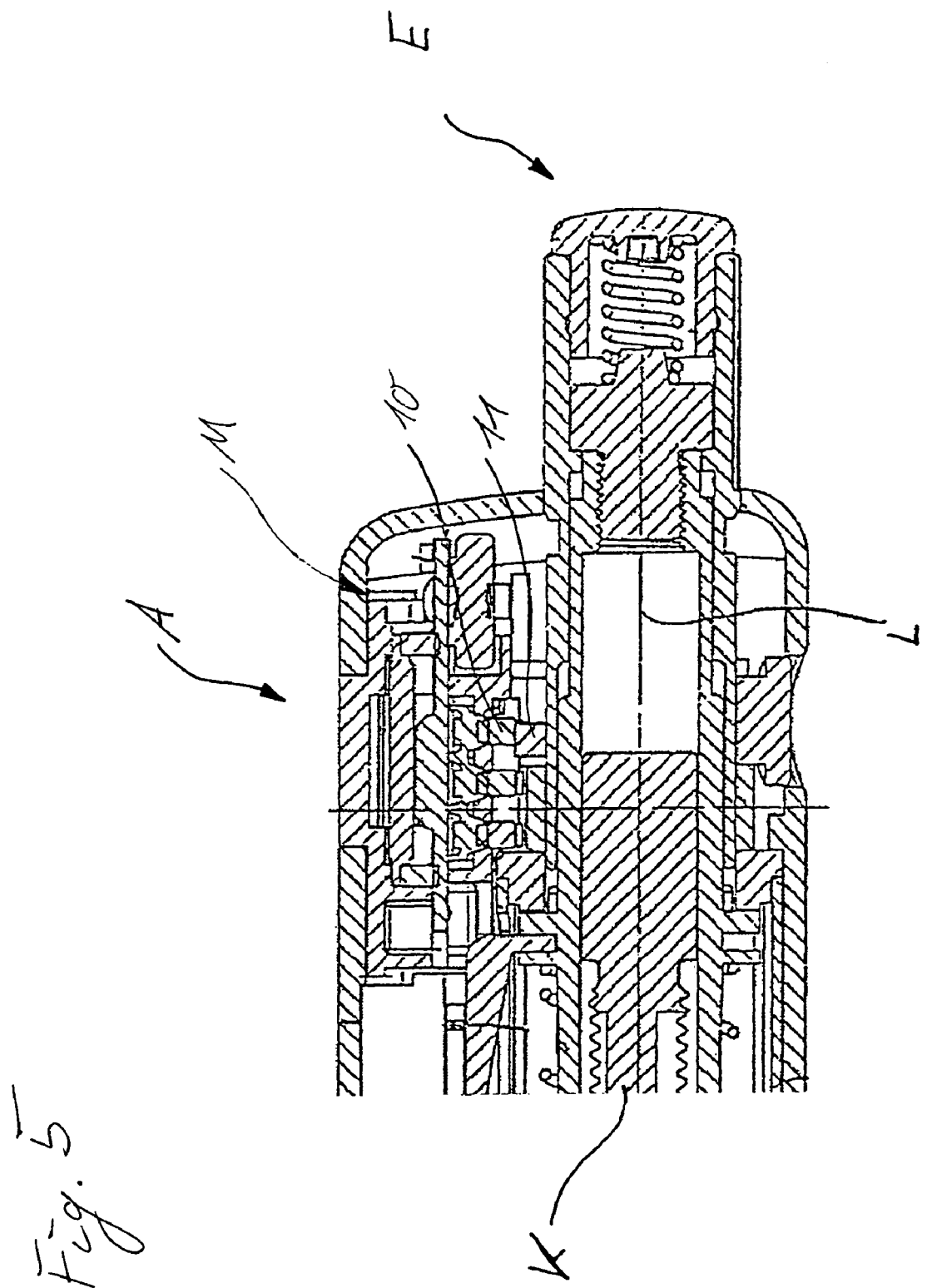
FIG. 5 is a longitudinal section of a rear portion of an injection apparatus.

FIG. 2 shows the module base shown in FIG. 1, with a silicone pad placed on it as a sealing element 3, wherein the silicone pad 3 comprises holes corresponding to the lower, larger outer diameters of the distancing bolts 2, such that the silicone pad 3 is positioned stationary on the module base 1 by the distancing bolts 2. The silicone pad 3 comprises an edge 3a which protrudes from the surface of the silicone pad 3, such that an area is defined by the surface of the silicone pad 3 and the edge 3a into which a circuit board 4 can be inserted. The silicone pad 3 is produced from an elastic, non-conductive material and has graphite pellets 5 on its surface which oppose contact points of the circuit board 4 to be subsequently attached, such that a pressure piece 10, slid through an opening 1d of the module base 1 by a cam ring 11, presses on the lower side of the silicone pad 3 and deforms it such that a graphite pellet 5 provided on the upper side of the silicone pad 3 is pressed upwards, to establish a contact on the circuit board 4.

A cavity is also provided in the silicone pad 3 for a battery compartment into which a graphite keg 6 is inserted in order to establish an electrically conductive contact with an upper side and as applicable a lower side of the battery. A venting channel 7 is provided between the battery compartment and the graphite pellets 5, such that the graphite pellets 5 can easily move back and forth without being obstructed in their free movement by pressure or suction effects. Equally, the venting channel 7 makes it easier to insert a battery into and remove a battery from the battery compartment.

FIG. 3 shows the device shown in FIG. 2, on which a circuit board 4 comprising a chip indicated in black has been placed. The distancing bolts 2 each have a partial piece in their upper area which has a smaller outer diameter approximately corresponding to holes in the circuit board 4, such that the circuit board 4 is positioned by the upper partial areas of the distancing bolts 2. The circuit board 4 is completely surrounded by the edge 3a of the silicone pad 3, whereby on the one hand, the circuit board 4 is protected from substances penetrating laterally and on the other hand, the battery—which is arranged beneath the circuit board 4 and inserted into the graphite keg 6—is completely sealed off or isolated. The battery contacts an electrode, provided on the lower side of the circuit board 4 in the area of the arrow P, via a contact provided on the battery and lying directly on the lower side of the circuit board 4. The outer side of the battery is connected via the graphite keg 6 to an approximately annular electrode which is likewise provided on the lower side of the circuit board 4 and is indicated by a broken line, such that the + and − poles of the battery can be electrically connected to the circuit board 4 in a simple manufacturing process, without soldering or contact bows.

The distancing bolts 2 can be fused, for example by ultrasound, and thus fix the circuit board 4 on the module base 1, such that the battery is pressed onto the lower side of the circuit board 4 by the silicone pad 3. The entire sub-assembly can subsequently be suitably programmed and configured, for example to a desired counting step.

FIG. 4 shows the sub-assembly shown in FIG. 3, with a module window casing 9 attached which comprises recesses 9a into which locking projections 1a of the module base 1 can lock, so as to fixedly connect the module window casing 9 to the module base 1 and thus ensure a secure seal. The module window casing 9 comprises a module window 8 which is at least partially transparent and beneath which an LCD display provided on the circuit board 4 (not shown in FIG. 3) can be provided.

Thus, by means of the module base 1 and the module window casing 9, the entire circuit board 4 including the battery can be encompassed and sealed off via the silicone pad 3, wherein the electrical contact between the battery and the circuit board 4 can be ensured, without an additional contact bow. This enables the height of the sub-assembly as a whole to be reduced, wherein, in one embodiment, the space thus gained can be used for an additional seal. The battery can thus be secured in the module without soldering, whereby nocuous lead is no longer used to produce the module.

In the foregoing description, embodiments of the invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A sealing element for substantially isolating an electrical component of an injection device from other components of the device, the injection device comprising a casing for supporting the electrical component, the sealing element comprising:
   a substantially continuous pad formed of an elastic, non-conductive material positioned between the casing and the electrical component, the pad comprising:
   a first side;
   a second side;
   an edge associated with the pad, the edge protruding from the first side of the pad and defining a recessed area for receiving the electrical component; and
   a cavity defined by the pad, the cavity extending from the first side through the second side of the pad;
   an electrically conductive element arranged in the cavity, the electrically conductive element configured for enabling electrical contact to be established between an electrical source at the second side of the pad and the electrical component at the first side of the pad; and
   a sensing element arranged in the first side of the pad, wherein the first side of the pad is configured to receive the sensing element, and the sensing element is located to oppose and be spaced from a contact point on the electrical component and further located to oppose a pressure piece on the second side of the sealing element, wherein contact of at least one pressure piece with the second side of the sealing element establishes contact between the sensing element and the contact point.

2. The sealing element as set forth in claim 1, wherein the sealing element comprises a single piece.

3. The sealing element as set forth in claim 1, wherein the sealing element cooperates with a portion of the casing to isolate the electrical component.

4. The sealing element as set forth in claim 1, wherein the electrical component is at least one of a circuit board and a chip.

5. The sealing element as set forth in claim 1, wherein the electrical source comprises a battery, and the casing comprises a recess for the battery and the electrically conductive element is arranged in the sealing element to enable establishing electrical contact between the battery and the electrical component.

6. The sealing element as set forth in claim 1, wherein the sealing element comprises a generally elastic portion.

7. The sealing element as set forth in claim 1, further comprising a venting channel in the first side of the pad adapted to allow free movement of the sensing element.

8. The sealing element as set forth in claim 1, wherein the sensing element protrudes from the first side of the pad.

9. The sealing element as set forth in claim 1, wherein the electrically conductive element comprises a keg configured to establish an electrical connection between the electrical source and the electrical component.

10. The sealing element as set forth in claim 9, wherein the electrical source is a battery and the keg comprises a generally cylindrical-shaped member having a bottom and an open top configured to receive the battery.

11. The sealing element as set forth in claim 1, wherein the injection device further comprises a module window casing configured for placement over the electrical component and for attachment to the casing.

12. The sealing element of claim 11, wherein the casing defines at least one hole and the at least one pressure piece is configured to be inserted through the at least one hole to contact the second side of the sealing element at the pressure point when actuated, and the injection device further comprises at least one actuator adapted to actuate the at least one pressure piece.

* * * * *